United States Patent [19]

Thomson

[11] 4,260,382

[45] Apr. 7, 1981

[54] AIR TURBINE DENTAL HANDPIECES AND SWIVEL CONNECTIONS THEREFOR

[76] Inventor: Loronzo H. Thomson, c/o Numerical Engineering Machine Company, P.O. Box 10248, Wilson Airport, Macon, Ga. 31201

[21] Appl. No.: 114,338

[22] Filed: Jan. 23, 1980

[51] Int. Cl.³ .............................................. A61C 1/08
[52] U.S. Cl. .................................. 433/126; 285/136; 433/29
[58] Field of Search ................. 433/126, 114; 285/136

[56] References Cited

U.S. PATENT DOCUMENTS

| 2,535,338 | 12/1950 | Wilcox | 433/126 |
|---|---|---|---|
| 3,521,359 | 7/1970 | Harris | 433/126 |
| 4,142,742 | 3/1979 | Corwett | 285/136 |
| 4,213,243 | 7/1980 | Flatland | 433/126 |

Primary Examiner—Robert Peshock
Attorney, Agent, or Firm—Roylance, Abrams, Berdo & Farley

[57] ABSTRACT

For a dentist's installation comprising a handpiece equipped with a turbine for driving a dental tool and flexible conduits leading to the handpiece to supply pressure fluid for driving the turbine, leading turbine exhaust fluid away from the handpiece, and supplying at least cooling water to be applied to the tooth, the invention provides an improved swivel arrangement effective to prevent forces from being applied by the flexible hoses to the handpiece. A face seal swivel is employed in a manner eliminating compression seals, such as gaskets or O-rings. In addition to passing fluids, the device can transmit light via the swivel so that the dental tool and tooth can be illuminated.

38 Claims, 29 Drawing Figures

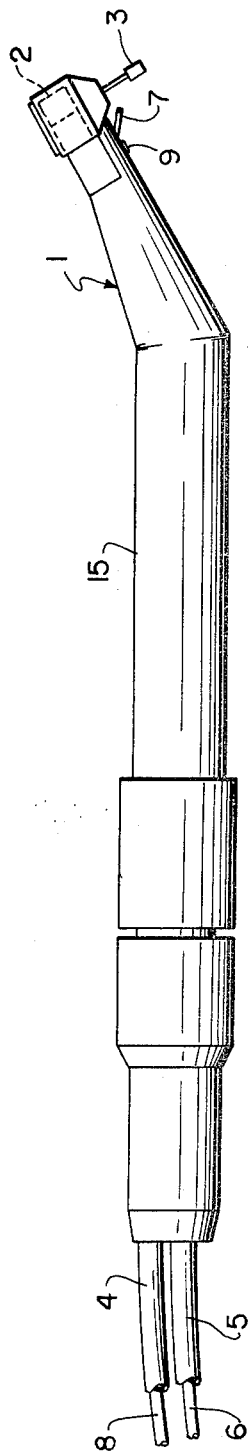
FIG. 1
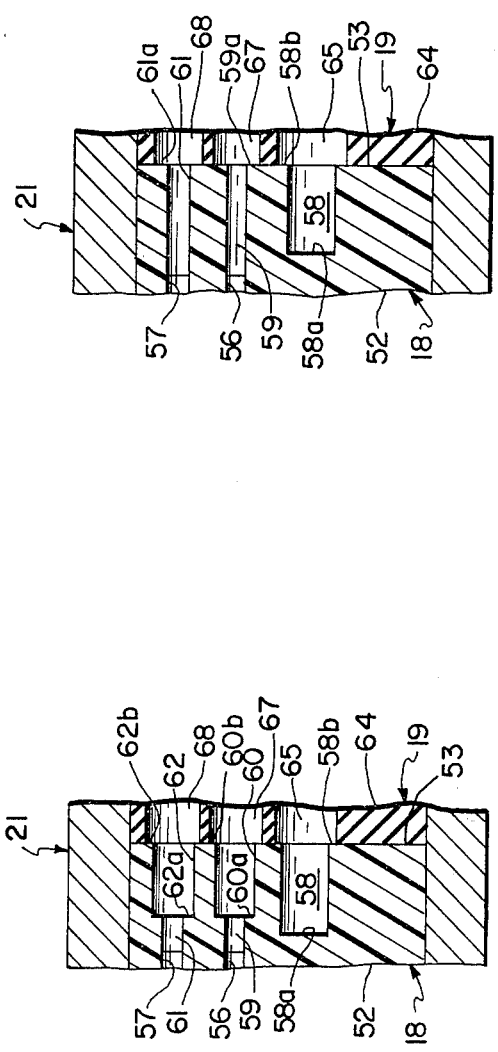
FIG. 8
FIG. 7

AIR TURBINE DENTAL HANDPIECES AND SWIVEL CONNECTIONS THEREFOR

BACKGROUND OF THE INVENTION

Commencing in the 1950's, belt drives for dental handpieces were largely replaced by miniature air turbines which operate at relatively high rotational speeds, the turbines for such handpieces being disclosed, for example, in U.S. Pat. No. 3,055,112, issued Sept. 25, 1962, to John V. Borden. Within a relatively few years, such handpieces were widely used and had advanced to the state where most dental handpieces had not only two hoses or tubes to carry air to and from the turbine but also separate water and air hoses to supply water and air separately for cooling the tooth being operated on with the handpiece. Dentists and prior-art workers noted early in the history of the air turbine handpiece that the hose bundle, when pressurized with air and water, acts as if it were alive, applying a varied and unpredictable torque to the handpiece during use. With the turbine driving a drill, the high speed of the drill makes the drill aggressive, fast and free cutting and it is therefore imperative that the dentist using the handpiece have a good and uninterrupted feel of the cutting forces applied at the tooth, else risk cutting away too much of the tooth or, out of caution, cutting too little. The effect of erratic and unpredictable forces, or changes of force, applied to the handpiece by the pressurized hose bundle is a significant disadvantage of handpieces equipped with an air turbine.

Because of the inconvenience and danger caused by the hose bundle of such dental handpieces, prior-art workers have endeavored to provide the handpiece with a multiple path flow swivel, as seen in:

| | |
|---|---|
| 2,884,695 | Ellis |
| 3,173,207 | Burzlaff |
| 3,709,630 | Pohl et al |
| 3,858,323 | Flatland |
| 3,894,338 | Loge et al |
| 3,921,296 | Harris |
| 4,075,761 | Behne et al |
| 4,080,737 | Fleer | and U.K. patent application No. GB 2,004,610 filed Apr. 4, 1979. Yet, despite such efforts, air turbine dental handpieces in use today do not have any effective means for swivelling the hose bundle in such a manner as to relieve the handpiece from forces, and particularly changes in forces, applied by the hose bundle. While some swivel attachments are offered, these require such a relatively high torque to operate the swivel that much of the force generated by the hose bundle is simply imparted to the handpiece via the swivel. A number of difficulties appear to have prevented prior-art workers from arriving at a satisfactory solution to the problem. One difficulty is simply the small size of the handpiece. Thus, the outer diameter of the handle of a typical handpiece is 0.62 inch, so that maximum inner diameters are on the order of 0.475 inch, and manufacturing tolerances for the parts of the swivel may be in the millionths of an inch. Next, if cooling air and water are supplied in addition to the air for driving the turbine, and if the exhaust air from the turbine is to be carried away by a hose, the problem of sealing the swivel is difficult, and prior-art approaches have required a plurality of seal elements. When adequate pressures are applied to the seals to prevent leakage, the torque required to turn the swivel becomes excessive. Efforts to solve the seal problem have resulted in manufacturing costs for the swivel so high as to be unrealistic. The problem is further complicated by the fact that the flow of air and water through the swivel tend to cool the parts of the swivel, resulting in dimensional changes which lead to leakage, jamming or erratic operation.

OBJECTS OF THE INVENTION

A general object of the invention is to provide an air turbine dental handpiece, and swivels for such handpieces, which are free from the adverse effects of the pressurized hose bundle.

Another object is to provide such a dental handpiece swivel that can be manufactured at an acceptable cost.

A further object is to provide such a device wherein the sealed joint necessary for swivelling the hose connections can be turned with low torque.

Yet another object is to provide such a device which is practical for manufacture in the relatively small size characteristic of dental handpieces.

Another object is to provide such a device in which the axial thrust generated by pulling the handpiece against the usual hose bundle retractor is accepted by low friction bearing means.

A still further object is to devise a way in which a conventional handpiece, even though delivered to the customer, can be modified according to the invention.

SUMMARY OF THE INVENTION

Devices according to the invention incorporate swivel connections in or on the handle of the handpiece which can conduct turbine air to and from the turbine and at least cooling water from the hose bundle to the location of the turbine in such fashion that full 360° rotation of the handle relative to the hose bundle is possible at torques on the order of, e.g., 1 in.-oz. or less. Two swivel members are employed, the first attached to the hose bundle to rotate therewith, the second secured against rotation relative to the handpiece. Multiple rotary seals are eliminated by having all flow passages of the first swivel member open through the front face of that member and all flow passages of the second swivel member open through the rear face of the second member. The front face of the first member and rear face of the second member are flat faces lying in planes at right angles to the axis of relative rotation between the two swivel members and are so disposed that the two faces are separated by from zero to 0.0005 inch. At least one of the two faces is provided with a plurality of concentric grooves centered on the axis of relative rotation and opening toward the other of the two faces, and communication through the swivel for each hose of the hose bundle is established through a different one of the grooves. In one embodiment, one of the two faces is of metal, the other face is of a low friction polymeric material, and spring means is provided to urge the two faces toward each other, one of the two swivel members "floating" relative to the handpiece, that is, being capable of very small movements at right angles to the axis of relative rotary movement, axially thereof and in a swinging mode about axes transverse to the axis of relative rotation, so that under the compliant biasing force of the spring means that member can adjust inherently to provide precise parallelism between the two faces. In another embodiment, both faces are of metal, and the two swivel members are secured against relative axial movement in positions such that an axial gap not exceeding 50 millionths of an inch exists between the faces when the device is at room temperature. In some advantageous embodiments, the flow passages through the two swivel members for the exhaust air from the turbine pass axially thrugh the centers of the two swivel members, thus communicating directly with each other rather than via one of the circular grooves. In other advantageous embodiments, providing illumination at the tooth via fiber optic bundles, the fiber optic bundles are accommodated by central through bores in the swivel members, or by a central through bore in the forward swivel member with the rear swivel member then containing the light source, all flow passages then communicating via the circular grooves.

IDENTIFICATION OF THE DRAWINGS

In order that the manner in which the foregoing and other objects are achieved according to the invention can be understood in detail, particularly advantageous embodiments of the invention will be described in detail with reference to the accompanying drawings, which form a part of the original disclosure of this application, and wherein:

FIG. 1 is a semidiagrammatic side elevational view of a dental handpiece according to the invention;

FIG. 7 is an enlarged fragmentary longitudinal sectional view taken generally on line 7—7, FIG. 6;

FIG. 8 is a view similar to FIG. 7 showing a modified form of the structure shown in FIG. 7;

Figure 2:
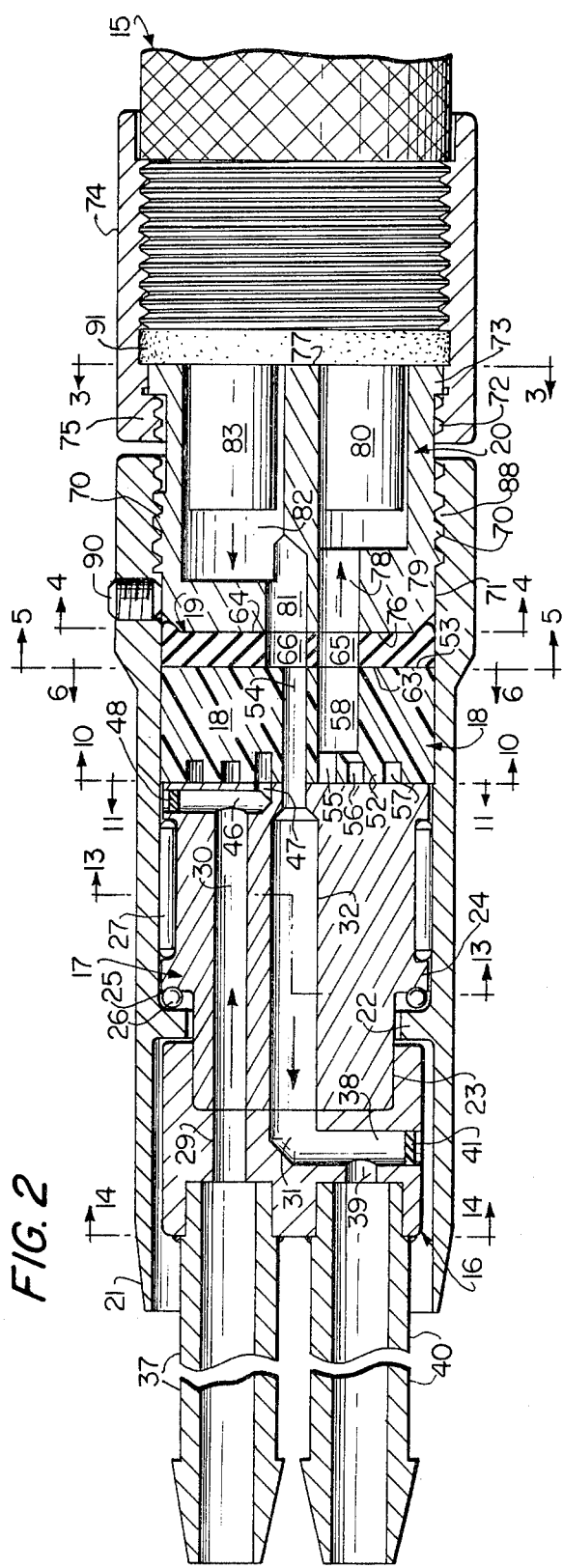
FIG. 2 is a longitudinal sectional view of the swivel and handpiece end of the device of FIG. 1.
Figure 10:
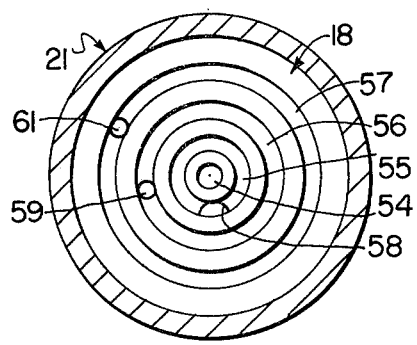
Figure 11:
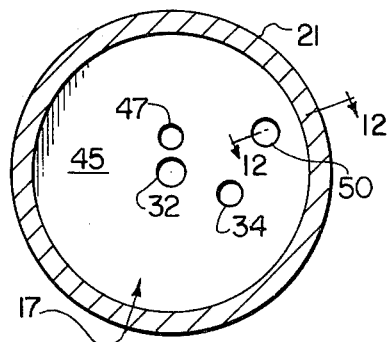
Figure 13:
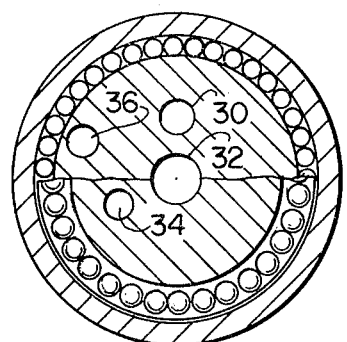
Figure 12:
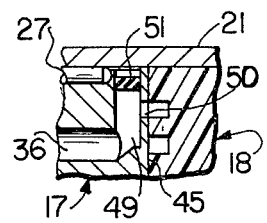
Figure 14:
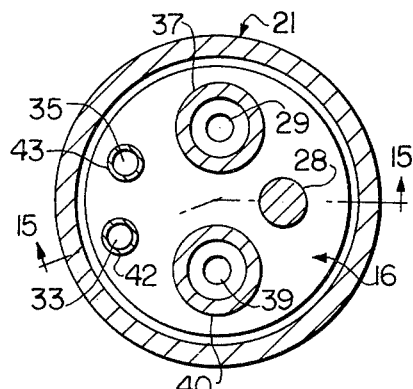
Figure 15:
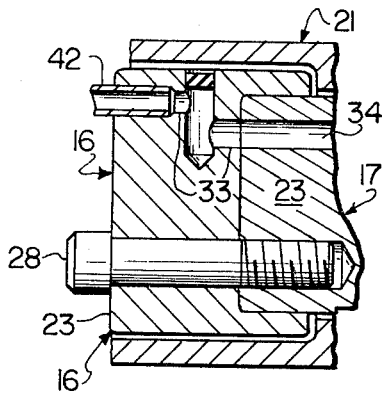
Figure 16:
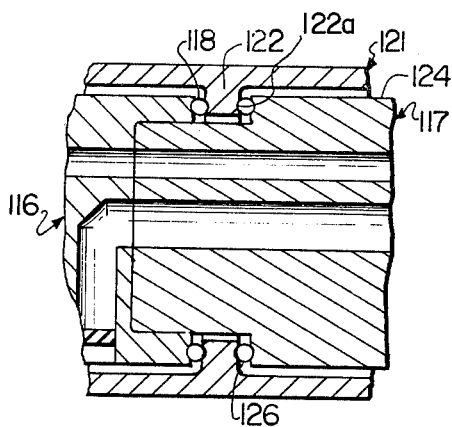
Figure 17:
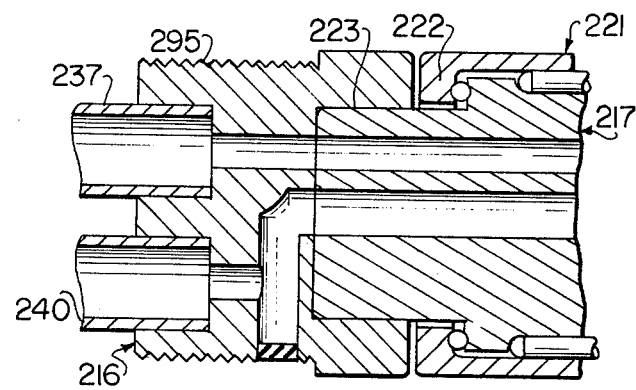
Figure 18:
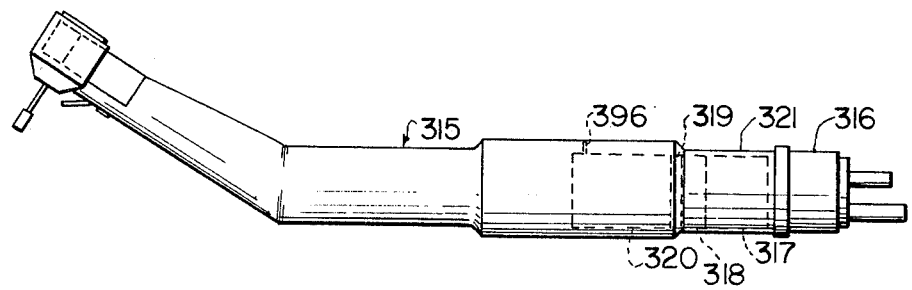
Figure 19:
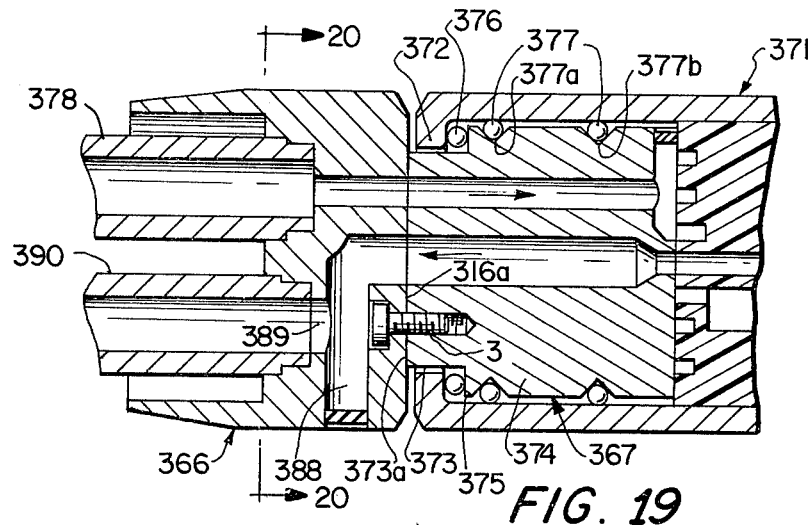
Figure 20:
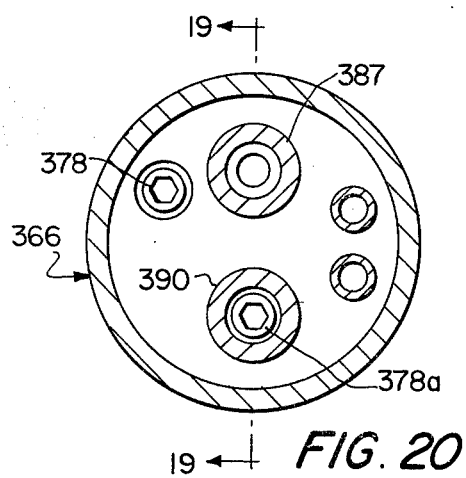
Figure 21:
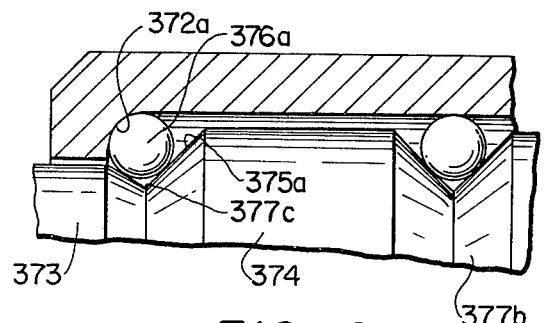
Figure 22:
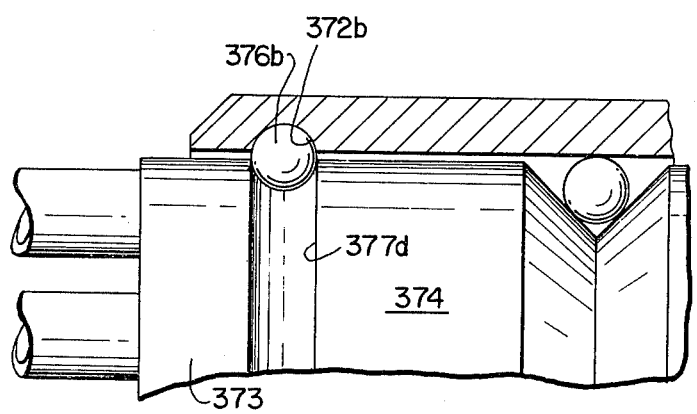
Figure 23:
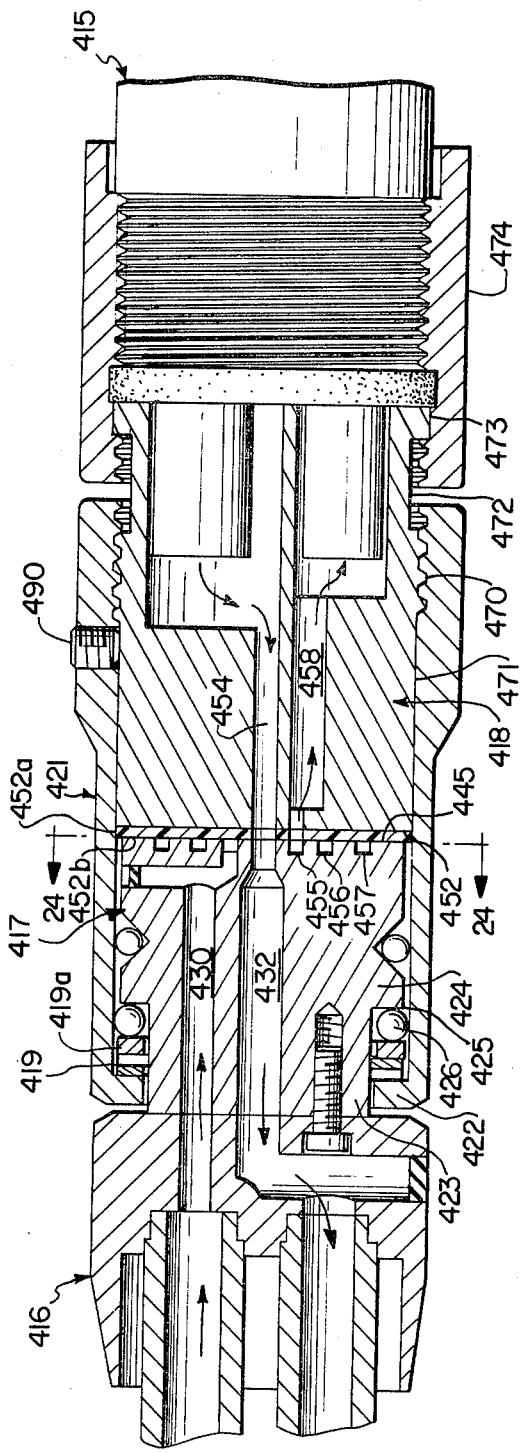
Figure 24:
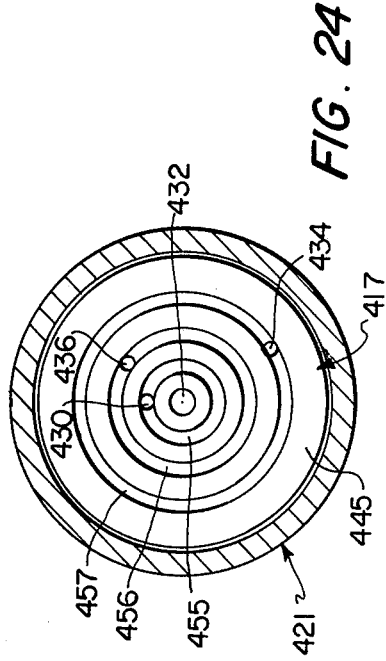
Figure 25:
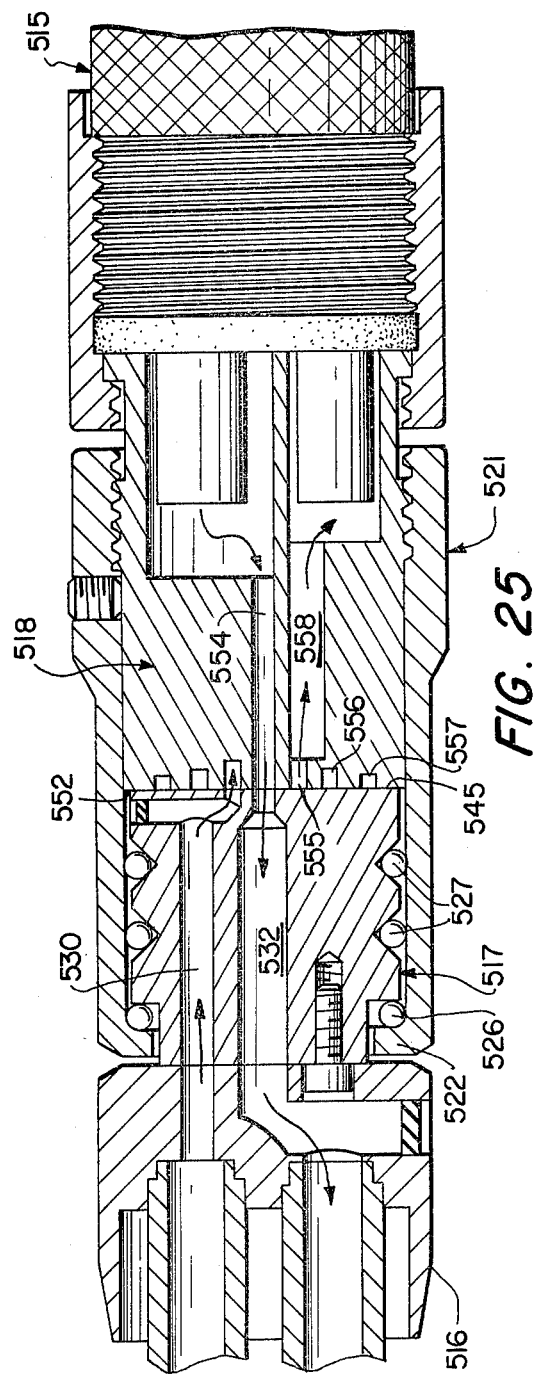
Figure 26:
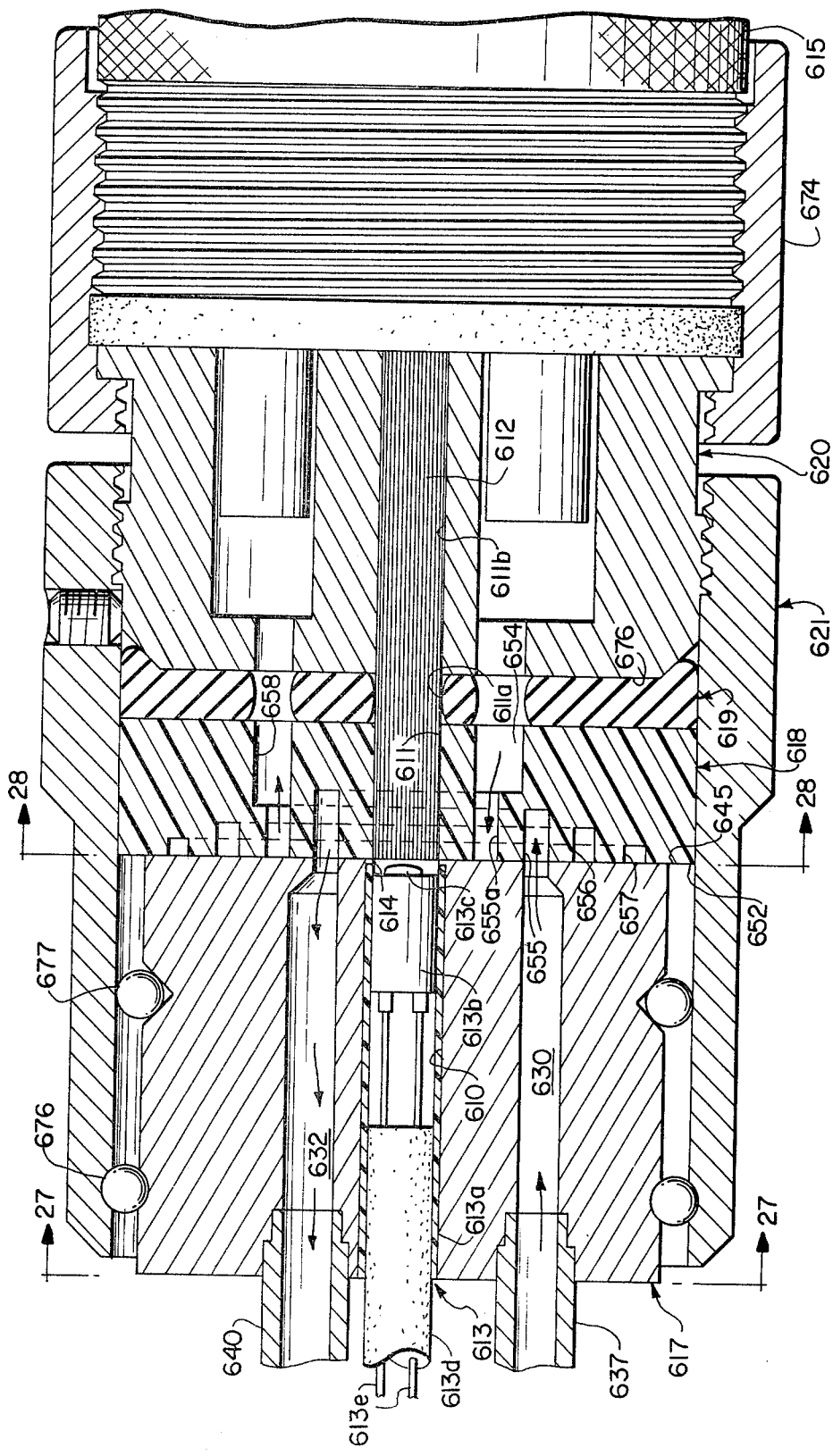
Figure 27:
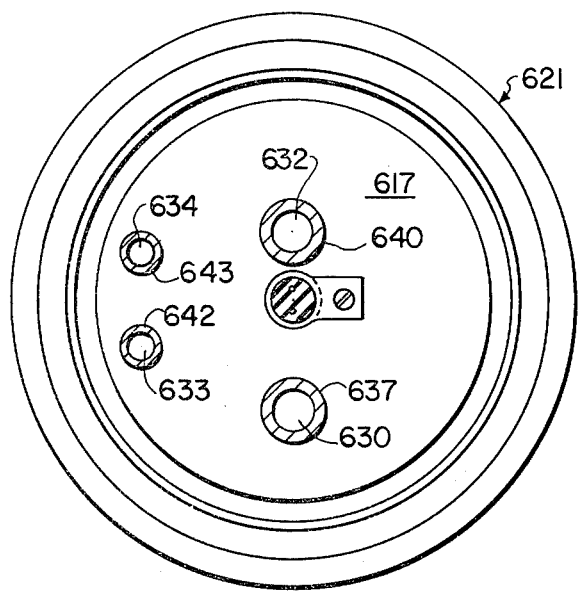
Figure 28:
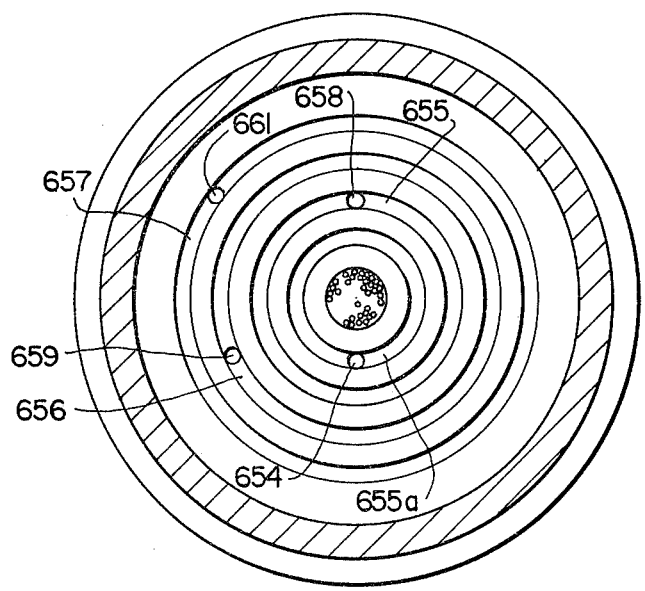
Figure 29:
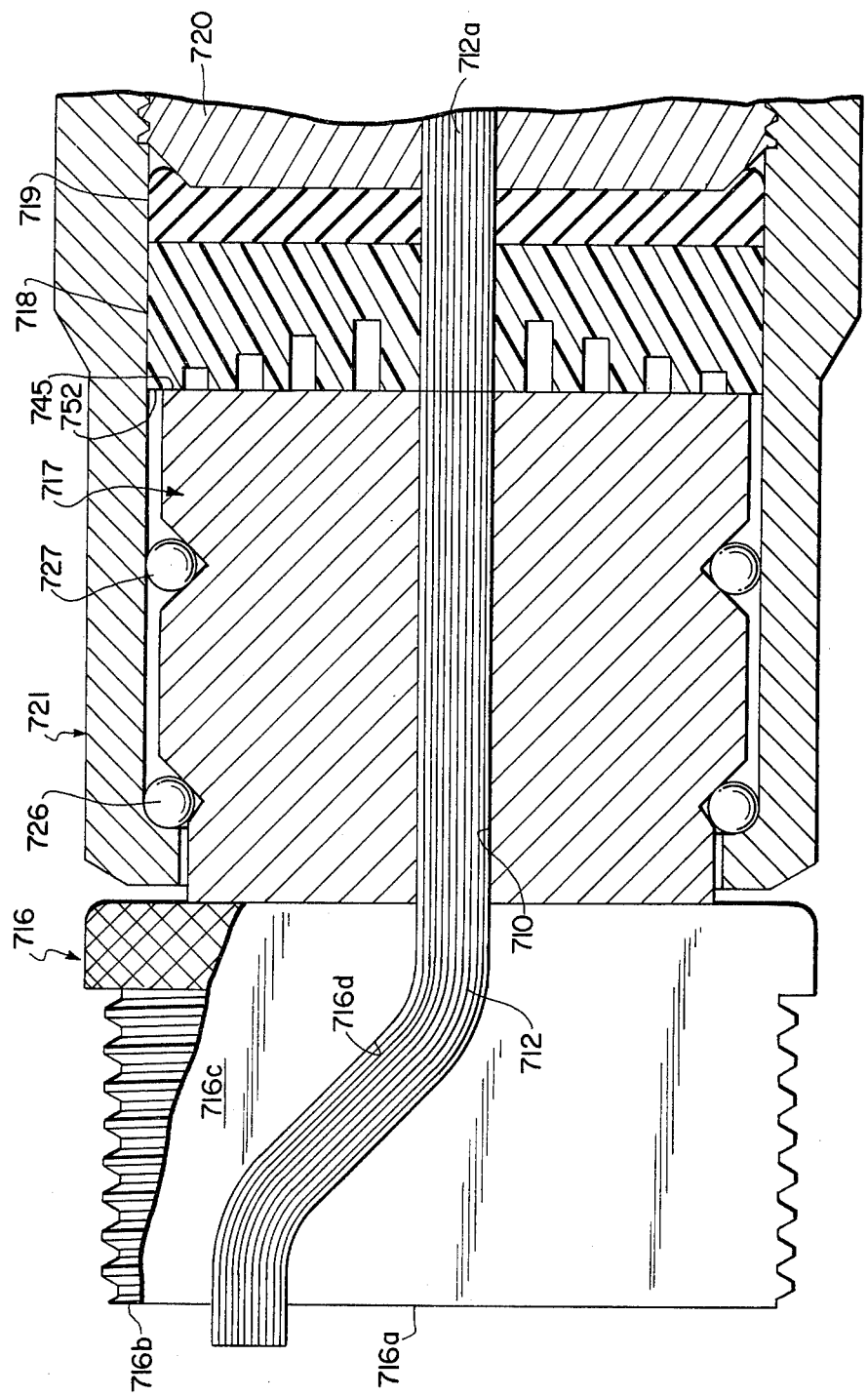

FIGS. 10 and 11 are transverse sectional views taken generally on lines 10—10 and 11—11, FIG. 2, respectively;

FIG. 12 is a fragmentary sectional view taken generally on line 12—12, FIG. 11;

FIGS. 13 and 14 are transverse sectional views taken on lines 13—13 and 14—14, FIG. 2, respectively;

FIG. 15 is a fragmentary longitudinal sectional view taken generally on line 15—15, FIG. 14;

FIG. 16 is a fragmentary longitudinal sectional view illustrating a modification of the bearing structure for the device of FIGS. 1-15;

FIG. 17 is a fragmentary longitudinal view illustrating another modification;

FIG. 18 is a side elevational view illustrating another embodiment of the invention;

FIG. 19 is a fragmentary longitudinal sectional view illustrating a further modification of the device of FIGS. 1-15;

FIG. 20 is a transverse sectional view taken generally on line 20—20, FIG. 19;

FIGS. 21 and 22 are fragmentary enlarged longitudinal sectional views illustrating other bearing structures useful according to the invention;

FIG. 23 is a view similar to FIG. 2 illustrating another embodiment of the invention;

FIG. 24 is a transverse sectional view taken generally on line 24—24, FIG. 23;

FIG. 25 is a view similar to FIG. 2 showing a further embodiment;

FIG. 26 is a view similar to FIG. 2 of yet another embodiment;

FIGS. 27 and 28 are transverse sectional views taken generally on lines 27—27 and 28—28, FIG. 26, respectively; and FIG. 29 is a fragmentary longitudinal sectional view illustrating a still further embodiment.

DETAILED DESCRIPTION OF FIGS. 1-15

Considering FIG. 1, the invention is illustrated as applied to a dental handpiece 1 having an air turbine 2 driving, e.g., a dental burr 3, the turbine being powered by compressed air supplied via hose 4 and conducted away by hose 5. Cooling water for the tooth being cut is supplied by hose 6 and discharged via a nozzle 7 offset slightly from the burr axis in the bottom of the turbine housing and tilted so as to be directed toward the active surface of the burr. Cooling air, separate from the turbine air, is delivered to the handpiece by hose 8 and can be projected onto the tooth either by a second nozzle 9, as shown, or by being discharged downwardly around the stem of the burr.

The handpiece includes the usual handle 15, with the hoses connected to the end of the handpiece opposite the turbine, and with the handle carrying, as best seen in FIG. 2, a hose connector 16, a first swivel member 17, a second swivel member 18, a resiliently compressible gasket 19, and an adaptor 20.

Turning to FIG. 2, it will be seen that, in this embodiment, the hose connector 16, first and second swivel members 17 and 18, gasket 19 and adaptor 20 are enclosed by a cylindrical tubular casing 21 having an inturned transverse annular flange 22 intermediate its length. First swivel member 17 is fabricated from hardened stainless steel and is of circular transverse cross section, including a rear end portion 23 of suitable dimension to pass through flange 22 and a larger diameter portion 24 which joins portion 23 in a transverse annular shoulder 25 facing flange 22. Shoulder 25 is formed with a raceway to accommodate ball bearings 26. The outer diameter of portion 24 is grooved circumferentially to accommodate needle bearings 27 which bear both against the wall of the groove and against the right cylindrical inner surface of the surrounding portion of casing 21. Member 17 and its bearings 26, 27 are installed with casing 21 upright and hose connector 16 is inserted downwardly into the casing so as to telescope over the projecting end of portion 23, the hose connector then being secured to member 17 by screw 28, FIG. 15. The rear face of member 17 and the front face of hose connector 16 are lapped ultra-flat surfaces. Hose connector 16 and member 17 have aligned straight bores 29 and 30, respectively, to conduct pressurized air for the turbine; aligned bores 31 and 32, respectively, for return air; aligned bores 33 and 34, respectively (FIGS. 14, 15 and 13), for cooling water; and aligned bores 35 and 36, respectively (FIGS. 14 and 13), for cooling air. Bore 29 of hose connector 16 opens directly into the rigid tubular shank 37 which is secured to and projects from the trailing face of connector 16. Bore 31 intersects a radial bore 38 which in turn intersects longitudinal bore 39, the latter bore opening into shank 40 for the turbine exhaust hose, the outer portion of bore 38 being plugged, as with epoxy, at 41. Bores 33 and 35 communicate with water hose shank 42 and air hose shank 43, FIG. 14, in the same manner just described.

The front face 45 of member 17 is lapped so as to be ultra-flat and lies at right angles to the axis of casing 21 when member 17 is in place. Bore 30 intersects radial bore 46 which in turn intersects a longitudinal bore 47 opening through face 45, the outer end of bore 46 being plugged, as with epoxy, at 48. Bore 32 is reduced in diameter adjacent face 45 and then opens through the center of face 45. Bore 34 is reduced in diameter before reaching face 45, then opens directly through that face. As seen in FIG. 12, bore 36 intersects a radial bore 49 which in turn intersects a longitudinal bore 50 which opens through face 45, the outer end of bore 49 being sealed, as with epoxy, at 51.

Second swivel member 18 is formed of low friction polymeric material, typically polytetrafluoroethylene, is right cylindrical, and has flat rear and front faces 52 and 53, respectively, both faces being lapped to ultra-flat condition. The diameter of member 18 is slightly smaller, typically two or three thousandths of an inch (0.025-0.075 mm.) smaller, than the inner diameter of the surrounding portion of casing 21. Member 18 can be made by injection molding with accuracy to assure that faces 52 and 53 are mutually parallel. The member is formed with a central through bore 54, and face 52 is provided with a series of three circular grooves 55-57, FIG. 10, each concentric with through bore 54, groove 55 being significantly deeper than grooves 56 and 55. Considering FIGS. 10 and 11, it will be apparent that apertures 47, 34 and 50 in the front face 45 of member 17 have diameters respectively equal to the radial widths of grooves 55-57 and are so located that aperture 47 registers with groove 55, aperture 34 registers with groove 56, and aperture 50 registers with groove 57 when rear face 52 of member 18 is registered with front face 45 of member 17. To conduct air forwardly from groove 55, member 18 is provided with a straight longitudinal bore 58 extending from groove 55 through front face 53. Bore 58 is of a diameter equal to about twice the radial width of groove 55 and is so located that the transverse cross section of the bore overlies the inner edge of the groove and crosses the outer edge. As seen in FIG. 7, cooling water is led forwardly from groove 56 by a small bore portion 59, which opens through the bottom of the groove, and a larger bore 60 which opens through front face 53. Similarly, cooling air is led forwardly from groove 57 by the combination of small bore 61 and large bore 62.

Figure 5:
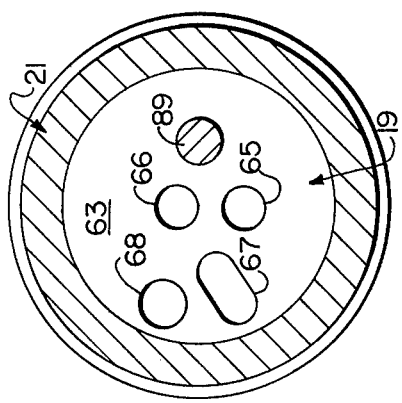

Gasket 19 is a relatively thick circular disc of soft elastomeric material, typically a soft rubber having a hardness (Shore A) of 35-70 or a synthetic rubber, e.g., neoprene, butyl or nitrile, having a hardness (Shore A) of 50-70. In its relaxed condition, the gasket has a diameter to be snugly embraced by casing 21 and a thickness, typically 1/16 in. (1.6 mm), adequate to provide a significant spring force when compressed, the rear and front faces 63, 64 being flat and mutually parallel when the gasket is relaxed. As seen in FIGS. 2 and 5, a bore 65 extends through the gasket, is of the same diameter as bore 58 and is so located that bore 65 forms a continuation of bore 58 in the assembled device. A second through bore 66, of the same size, is provided to communicate with bore 54, bore 66 being offset from bore 54 in the assembled device in such fashion that the circumferences coincide at one point and bore 54 therefore opens fully into bore 66. Cooling water from bore 60 of member 18 is conducted forwardly through gasket 19 by a radial slot 67 which, in the assembled device, extends outwardly from the location of bore 60 to overlap bore 84 of adaptor 20, the inner and outer ends of the slot being circular and of a diameter equal to that of the bores with which the slot is to communicate. A through bore 68 is provided to conduct cooling air through gasket 19, bore 68 being located to register with bore 62 of member 18.

From FIGS. 2 and 5-7, it will be noted that surface portions of member 18 are provided which face forwardly, are substantially equal to the plan area of grooves 55-57 respectively, and are exposed to the pressure of fluid passing through the swivel members. Thus, the fact that the diameter of bore 58 is larger than the radial width of groove 55 provides surface 58a, FIGS. 2 and 6, and the fact that the diameter of opening 65 is larger than that of bore 58 exposes an additional surface portion 58b, FIGS. 2 and 7. Similarly, enlargement of bore 60 provides a surface 60a, FIG. 7, and enlargement of opening 67 relative to bore 60 provides an additional surface portion 60b, FIG. 7. Enlargement of bore 62 provides surface 62a, and larger opening 68 exposes additional surface portion 62b. Alternatively, as seen in FIG. 8, smaller diameter bores 59, 61 can continue completely through member 18, the surface portions to compensate for grooves 56, 57 then being at 59b and 61b, respectively.

Figure 3:
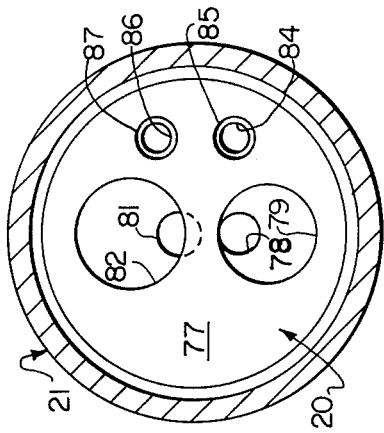
FIGS. 3-6 are transverse sectional views taken generally on lines 3—3, 4—4, 5—5 and 6—6, FIG. 2, respectively.
Figure 4:
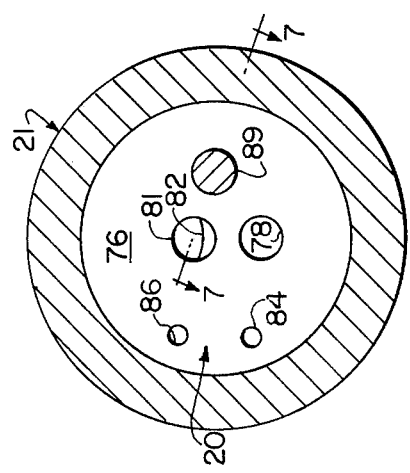
Figure 6:
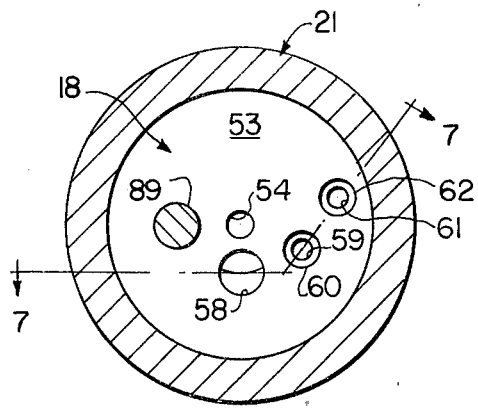
Figure 9:
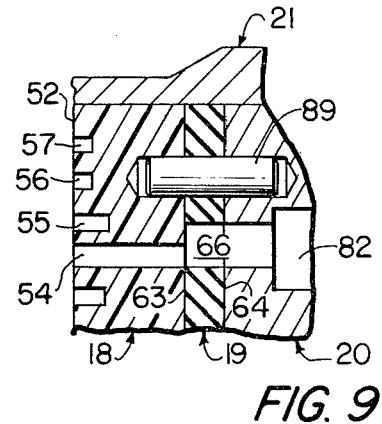
FIG. 9 is a fragmentary longitudinal sectional view taken generally on line 9—9, FIG. 4.

As shown in FIGS. 2-4, adaptor 20 is externally threaded for a portion of its length at 70 and has a plain right cylindrical outer surface 71, behind threads 70, a second plain right cylindrical outer surface 72, ahead of threads 70, and a transverse annular outwardly projecting shoulder 73 at its forward end. A nut 74 is provided to secure the assembly to the handle 15 of the handpiece. Nut 74 has an inwardly directed transverse annular end flange 75 which is internally threaded to mate with threaded portion 70 of the adaptor so that, before installation of the adaptor, nut 74 can be run forwardly over threaded portion 70 and thus be in position to engage shoulder 73 of the adaptor. Formed of stainless steel, adaptor 20 has a flat rear face 76 and flat front face 77, the two faces being mutually parallel and at right angles to the axis of the adaptor.

To conduct turbine air forwardly through the adaptor, a longitudinal bore 78 opens through rear face 76, bore 78 having the same diameter as bore 65 of gasket 19 and being located to register therewith. Bore 78 opens forwardly into an enlarged through bore 79 which in turn opens through front face 77 and is of a diameter to loosely accommodate the usual tubular turbine input shank 80 of the handpiece 1. Similarly, a longitudinal bore 81 opens through rear face 76 in a location to register with bore 66 of gasket 19 in the assembled device. Forwardly, bore 81 opens into an enlarged longitudinal bore 82 which in turn opens through front face 77 of the adaptor. Bore 81 is of the same diameter as bore 66. Bore 82 is of a diameter adequate to loosely accommodate the tubular turbine exhaust shank 83. Cooling water is conducted from the outer end of slot 67 in gasket 19, via a longitudinal bore 84, which in turn opens into a larger diameter bore 85, FIG. 3, opening through front face 77. Similarly, cooling air is conducted from bore 68 in gasket 19 through the adaptor by the combination of smaller longitudinal bore 86 and larger longitudinal bore 87. Bores 85, 87 respectively accommodate the tubular shanks (not shown) via which the cooling water and air are connected to the usual ducting which carries the water and air forwardly to the location of the turbine and burr.

At its forward end, casing 21 is provided with an internally threaded portion 88 capable of meshing with threaded portion 70 of adaptor 20. Member 18, gasket 19 and adaptor 20 are held in properly registered positions relative to each other by a dowel pin 89, FIGS. 4–6, which passes through a bore in gasket 19 and is engaged in blind bores in members 18 and 20. Since grooves 55–57 are circular and concentric with the central axis of member 18, bores 32, 54 are at the central axis of the assembly, and bores 34, 47, 50 are each located on member 17 to register with a different one of grooves 55–57, special care is not required to mate member 18 with member 17 during the assembly. Accordingly, when members 16 and 17 have been installed in casing 21, and members 18–20 have been assembled on dowel pin 89, the assembly of members 18–20 can be inserted into the casing with relative rotation to make up threaded portions 70 and 88. Tightening of threaded portions 70, 88 urges the grooved rear face 52 of member 18 firmly against front face 45 of member 17 and also applies an axial compressive force on gasket 19, that force being adjustable according to how far the threaded portions are made up. To provide space to accommodate compression of gasket 19, the periphery of adaptor 20 at rear face 76 is chamferred, as seen at 76a, FIG. 2, so as to provide an annular cavity of triangular radial cross section into which the gasket can intrude when the adaptor is threaded into the casing. When the desired spring force has been established in gasket 19, a set screw 90, FIG. 2, provided in a threaded radial bore in casing 21 in a location to be occupied by outer surface portion 71 of adaptor 20, is tightened to secure the adaptor rigidly to the casing. Axial compressive forces applied to members 17–18 remain because member 17 is in thrust engagement with bearing balls 26 and flange 22. The assembly is then completed by installing the usual gasket 91 and making up the threaded connection between nut 74 and the end of handle 15 of handpiece 1 until gasket 91 is placed under adequate compression to seal.

Casing 21, swivel member 17 and adaptor 20 are of the same metal, advantageously hardened stainless steel, and therefore have the same thermal coefficient of linear expansion. Accordingly, the axial space between front face 45 of swivel member 17 and rear face 76 of adaptor 20 does not change significantly as the parts are cooled by flow of air and water through the swivel. Though swivel member 18 is of a polymeric material having a much higher thermal coefficient of linear expansion than does stainless steel, so that member 18 tends to shrink away from member 17 as the parts are cooled, gasket 19 is made sufficiently thick to allow establishment of a spring force, by compressing the gasket, adequate to keep face 52 of member 18 lightly engaged with face 45 of member 17 despite axial shrinkage of member 18 as a result of cooling. This effect of the spring force of gasket 19 is possible because, with the diameter of member 18 slightly smaller than the inner diameter of casing 21, member 18 floats axially relative to the casing. Thus, in this embodiment, the front face of member 17 and rear face of member 18 are maintained in light rubbing contact under all temperature conditions normally encountered in a dentist's office.

OPERATION OF THE EMBODIMENT OF FIGS. 1–15

In operation, the dental handpiece with swivel connections is employed in conjunction with the usual foot pedal-controlled 4-hose hose bundle. All that is required to prepare the handpiece for use is to properly attach the four hoses of the bundle to the respective tubular shanks of hose connector 16. When the pedal is operated to supply pressurized air, the pressurized air flows forwardly through shank 37 into bore 29 of the hose connector and then through bores 30, 46 and 47 of member 17 into inner groove 55 of member 18. From groove 55, the pressurized air flows through the series combination of enlarged bores 58, 65, 78 and 79 and thence into the turbine inlet shank 80 of the handpiece. The conventional ducting of the handpiece leads the pressurized air to the inlet of turbine 2 and also leads the exhaust air from the turbine rearwardly through the handle of the handpiece, with the exhaust discharging from shank 83 into bore 82. From this point, the exhaust air flows rearwardly via bores 81, 66 and 54, then into bore 32 of member 17, and then via bores 31, 38 and 39 to discharge from shank 40 into the exhaust hose. Cooling water is supplied, at the command of the foot pedal, by water hose 6 attached to shank 42 and flows forwardly through duct 33, FIG. 15, and bore 34 into groove 56 of member 18, thence forwardly through bores 59 and 60, FIG. 7, of member 18, slot 67 of gasket 19, and bores 84 and 85 of adaptor 20 into the cooling water shank of the handpiece, being delivered then by the conventional ducting of the handpiece through nozzle 7 onto the tooth being cut. Cooling air is supplied on demand from hose 8 into shank 43, FIG. 14, thence forwardly via bores 35, 36 and 49 to escape via bore 50 into circular groove 57 of member 18. From groove 57, the air traverses bores 61, 62, 68, 86 and 87 to enter the cooling air shank of the handpiece and then be delivered by the conventional ducting of the handpiece to nozzle 9 and thus be applied to the tooth on which work is being done.

Throughout use of the handpiece, no significant torque is applied to handpiece 1 by the hose bundle. Even under full load of pressurized turbine air, cooling water and cooling air, any twisting motion which results in the hose bundle only causes rotation of the combination of members 16 and 17, as a unit, relative to casing 21, members 18–20 and handpiece 1, all acting as a unit. Similarly, if the dentist desires to rotate the handpiece generally about its longitudinal axis, the hose bundle cannot act to resist that turning motion, since the combination of the handpiece and members 18–21 is essentially free to be rotated relative to the hose bundle. As a result, the dentist's precision is increased, and the tendency for the dentist to become fatigued as a result of forces applied by the hose bundle is reduced.

Success of the invention arises from the fact that face 45 of swivel member 17 and face 52 of swivel member 52 are maintained in sealing engagement by only the relatively small compressive force applied by gasket 19, that the flush engagement between faces 45 and 52 generates only small frictional resistances and is completely independent of forces resulting from pulling the handpiece against the hose bundle. Being of hardened stainless steel and finished by a lapping operation, face 45 is an ultra-flat, smooth surface. Similarly, face 52 is a lapped ultra-flat surface. Since the diameter of member 18 is slightly smaller than that of the surrounding casing, member 18 has a limited freedom of lateral movement and tilting movement allowing it to adjust for any residual imperfections in faces 45, 52.

It has been found that presence of grooves 55–57 tend to create a significant axial force, equal to the areas of the grooves times the pressures of air and water in the grooves, tending to force members 17 and 18 apart. In the embodiment described with reference to FIGS. 1-15, that separating force is essentially eliminated, since the sum of surfaces 58a and 58b is approximately equal to the area of groove 55, that of surfaces 60a and 60b is approximately equal to the area of groove 56, and that of surfaces 62a and 62b is approximately equal to the area of groove 57, and the pressure downstream of face 52 therefore generates forces which act rearwardly on member 18 to counterbalance the separating forces. A pressure balance is similarly achieved between larger opening 66 and the larger diameter portion of bore 32 for the turbine exhaust. Accordingly, the extent to which gasket 19 is compressed to generate the spring force necessary for sealing at faces 45, 52 need not be increased to compensate for the separating forces generated by pressure in grooves 55–57.

It will be noted that the face seal at 45, 52 also serves as a thrust bearing for loads applied forwardly to swivel members 17, 18 and depends solely upon the low friction polymeric face 52 for lubricity. With balls 26 and needles 27 of hardened stainless steel, lubrication of the ball and needle bearings is not required.

In the modification shown in FIG. 16, the device is equipped with a second set of ball bearings 118 engaged between flange 122 of the casing and the front face of hose connector 116. Balls 118 are retained by an accommodating race in hose connector 116. Balls 126 remain as described with reference to FIGS. 1–15. Casing 121 is formed of hardened stainless steel, and swivel member 117 is again formed of hardened stainless steel so that, with the larger diameter portion 124 of member 117 loosely embraced by the hardened stainless steel casing, the needle bearings of the embodiment of FIGS. 1–15 can be eliminated by providing the bearing race 122a on the front face of flange 122 to coact with balls 126. The embodiment of FIG. 16 has the advantage that no axial thrust forces acting forwardly are applied to the face seal between the two swivel members.

In the field today, dentists have a large number of installations in which the hose bundle terminates in a hose connector adapted to be threadedly connected to the end of the handpiece. To accommodate the invention to those installations, casing member 221, FIG. 17, can terminate at inwardly directed flange 222, and a hose connector 216 can be secured to rearwardly projecting portion 223 of swivel member 217. Hose connector 216 is externally threaded at 295 and provided with tubular shanks, as at 237 and 240, in all respects identical to the shanks projecting from the end of the handle of the handpiece.

THE EMBODIMENT OF FIG. 18

As shown in FIG. 18, casing 321 can be made as an integral part of the handle 315 of the handpiece, the adaptor 320 being rigidly secured to the handle, e.g., by a radial pin at 396. Gasket 319, swivel member 318 and swivel member 317 remain the same as the corresponding elements in the embodiment of FIGS. 1–15. Hose connector member 316 is constructed and arranged as member 216, FIG. 17, so that a hose bundle with a standard hose connector can be attached.

THE EMBODIMENT OF FIGS. 19 and 20

As seen in FIG. 19, the rearward portion of casing 371 can terminate in transverse annular inwardly directed flange 372 and the first swivel member 367 can be supported in the casing entirely by ball bearings. Member 367 again has a main body portion 374 of larger diameter and a rearwardly projecting smaller diameter portion 373 which, in the assembled device, extends rearwardly through the opening defined by flange 372 and terminates in a flat end face 373a lying in a plane at right angles to the axis of relative rotation. End face 373a is disposed immediately adjacent the rear end face of the casing, as shown. Portions 373 and 374 are joined by transverse annular rearwardly facing shoulder 375 which is flat, i.e., not grooved as a ball race. A plurality of bearing balls 376 are disposed between the flat front face of flange 372 and shoulder 375, balls 376 having a diameter significantly smaller than the radial distance between the right cylindrical outer surface of portion 373 and the surrounding wall of casing 371, so that the antifriction bearing constituted by flange 372, shoulder 375 and balls 376 acts as a thrust bearing.

The right cylindrical outer surface of portion 374 is of a diameter slightly smaller than the inner diameter of the surrounding casing wall and is interrupted by two transverse annular V-grooves 377a and 377b, the side walls of the grooves being 45° frustoconical surfaces opposed to each other. Grooves 377a and 377b accommodate bearing balls 377c which are advantageously of the same diameter as balls 377 and are engaged between the surrounding right cylindrical inner surface of casing 371 and the walls of the respective grooves so that the grooves, the surrounding casing wall and the balls constitute a dual radial ball bearing which establishes the axis of relative rotation between member 367 and casing 371. Forwardly of swivel member 367, the device can be made as illustrated in FIG. 2.

The device includes a hose connector 366 generally like connector 16, FIG. 2, but having a single ultra-flat front surface 316a. Hose connector 366 is rigidly secured to swivel member 367 by two socket head screws 378 and 378a, FIG. 20, in such manner that surface 316a of the hose connector and rear end face 373a of the swivel member are clamped in flush engagement. Surface 316a and end face 373a are both lapped surfaces and, with the two screws being spaced apart along a chord of the circular periphery of face 373a, the two faces are engaged in such fashion as to require no sealing gasket. Hose connector 366 is equipped with two tubular hose connector shanks 387 and 390 in the same manner as described with reference to shanks 37 and 40, FIG. 2. Shank 390 is coaxial with bore 389 of member 366, bore 389 opening into cross bore 388 and being aligned coaxially with the threaded bore in swivel member 367 for screw 378a. The socket head of screw 378a is slightly smaller than the inner diameter of shank 390 and the inner diameter of bore 389, so that screw 378a can be passed through shank 390 and bore 389 when the hose connector is being attached to the swivel member.

BEARING ARRANGEMENTS OF FIGS. 21 AND 22

The ball bearing embodiment of FIG. 19 can be modified, as seen in FIG. 21, to eliminate one of the three sets of bearing balls. Thus, the inturned end flange of the casing can be formed with a radius at 372a and the shoulder between portions 373 and 374 of the swivel member is replaced by a V-groove 377c, so that the V-groove has one larger frustoconical side wall 375a opposed to radius 372a. Bearing balls 376a are engaged between the walls of groove 377c, on the one hand, and the curved raceway presented by the radius at 372a and the adjacent portion of the wall of the casing, on the other hand, so that the resulting ball bearing acts both in thrust and radially. Groove 377b and its associated bearing balls remain as described with reference to FIG. 19 and coact with the surrounding casing wall in radial bearing fashion.

The structure can be further modified, as shown in FIG. 22, in such fashion that portions 373 and 374 of the first swivel member have the same diameter and the casing has no inturned flange. Groove 377d is of arcuate radial cross section with the diameter of the arc matching that of the bearing balls 376b disposed in the groove. The casing is provided with a transverse annular inwardly opening groove 372b having the same arcuate radial cross section as does groove 377d. Bearing balls 376b are engaged between the walls of the two raceway grooves, so that the ball bearing acts in the radial mode and also acts to prevent relative axial movement between the casing and the first swivel member. Groove 377b and its associated bearing balls remains as previously described.

THE EMBODIMENT OF FIGS. 23 AND 24

As seen in FIG. 23, another embodiment of the invention again employs a tubular casing 421 of hardened stainless steel, a first swivel member 417 of hardened stainless steel disposed in the casing in such manner that relative rotation between the swivel member and the casing can occur about the common longitudinal central axis of the casing and swivel member, and a hose connector 416 secured to the rear end of the first swivel member in the manner described with reference to FIGS. 19 and 20. Member 417 again has a larger diameter main body portion 424 and a smaller diameter portion 423, the former having a diameter only slightly smaller than the inner diameter of the surrounding portion of the casing, the latter projecting freely through the opening defined by inturned end flange 422 of casing 421. Portion 423 is relatively long, so that when the rear end face of portion 423 is located just beyond flange 422, the shoulder 425 between portions 423 and 425 is spaced a substantial distance forwardly from flange 422. The space between flange 422 and shoulder 425 is occupied by a spring washer 419, a flat rigid washer 419a and a plurality of bearing balls 426, the arrangement being such that the opposed flat faces of shoulder 425 and washer 419a constitute raceways between which balls 426 are engaged. Spring washer 419 is of conventional form, bent in repeated-hill-and-dale configuration throughout its circular extent, so as to be resiliently compressible axially of the device when an axial force tends to decrease the space between flange 422a and washer 419a. Forwardly of shoulder 425, member 417 has a transverse annular V-groove to accommodate bearing balls 427 which are engaged between the walls of the groove and the surrounding wall of casing 421.

In this embodiment, the second swivel member 418 extends from the front face 445 of member 417 forwardly to the rear end of handle 415 of the handpiece and serves the purposes of both elements 18 and 20, FIG. 2. Member 418 comprises a main body of the same hardened stainless steel as casing 421 and first swivel member 417, the main body having a first right cylindrical outer surface 471 directly embraced by the casing, a threaded portion 470 engaged with internal threads at the forward end of the casing, a second right cylindrical portion 472 forwardly of the threads, and a transverse annular outwardly projecting flange 473. Member 418 is fixedly secured to casing 421 by the combination of the threads at 470 and a set screw 490 in the same manner as adaptor 20 is secured in the embodiment shown in FIG. 2. Attachment to handpiece handle 415 by nut 474 is accomplished in the same manner described with reference to FIG. 2. Member 418 has a flat rear face 452 to which is secured, as by molding, bonding or coating, a relatively thin layer 452a of low friction polymeric material, advantageously polytetrafluoroethylene, which in turn presents a lapped ultra-flat rear face 452b which lies in a plane at right angles to the axis of relative rotation between casing 421 and member 417.

First swivel member 417 is provided with a through passage 430 to conduct pressurized air forwardly, a central through bore 432 to conduct exhaust air rearwardly, a through passage 434, FIG. 24, to conduct cooling water forwardly, and a through passage 436 to conduct cooling air forwardly. The front face 445 of member 471 is provided with a plurality of circular grooves 455–457 which are concentric with the axis of relative rotation. While through bore 432 opens forwardly directly through the center of face 445, passage 430 opens through the bottom wall of groove 455 and passages 434 and 436 open respectively through the bottom walls of grooves 456 and 457, as will be clear from FIG. 24.

Second swivel member 418 has a central passage 454 which continues through polymer layer 452a so as to communicate directly with bore 432 of member 417. Similarly, member 418 has a passage 458 which communicates through an opening in layer 452a with groove 455, so that air from passage 430 of member 417 is delivered to passage 458 of member 418 via groove 455. Member 418 is similarly provided with two additional flow passages (not shown) to convey cooling air and cooling water, respectively, forwardly to the handpiece. Communication between the four flow passages of member 418 and the conventional ducting of the handpiece is established in the same manner described with reference to FIGS. 2 and 3.

When member 418 is installed in casing 421, the threads at 470 are made up until faces 445 and 452 are in rubbing contact and member 417 is moved slightly rearwardly relative to the casing so as to compress spring washer 419, thus establishing a spring force adequate to maintain faces 445 and 452 in rubbing contact under normal conditions of operation and, in all events, to prevent faces 445 and 452 from separating by more than 0.0005 inch. It will be noted that, in this embodiment, it is the first swivel member which floats relative to the casing so as to be axially movable, while the second swivel member is fixed. The device of FIG. 23 has the advantage that the axial dimension of polymeric member 452a is minimized, and the effect of the greater thermal coefficient of linear expansion of the polymeric material, as compared to steel, is therefore also minimized.

THE EMBODIMENT OF FIG. 25

In the embodiments shown in FIGS. 1–24, the active faces (e.g., faces 45 and 52 of the embodiment seen in FIGS. 1–15) of the two swivel members are maintained in light rubbing contact as a result of the structure employed and the fact that one swivel member floats relative to the casing and is urged resiliently toward the other swivel member, any separation of the two active faces which may occur under extreme conditions of, e.g., temperature change, being limited to a gap less than will allow escape of water. FIG. 25 illustrates an embodiment in which the active faces of the two swivel members are not maintained in rubbing contact but rather are spaced apart by an extremely small distance, advantageously not exceeding 50 millionths of an inch, under all operating conditions, the effect then being similar to that encountered in hydrostatic bearings, i.e., if present between the two surfaces, water cannot escape under the pressures involved.

This embodiment of the device comprises a tubular casing 521 of hardened stainless steel, a first swivel member 517 and a second swivel member 518, members 517 and 518 being of the same material as the casing. Casing 521 has an inturned end flange 522 and first swivel member 517 has the same configuration as that seen in FIG. 19, so that member 517 can be rotatably supported in the casing by thrust bearing balls 526 and radial bearing balls 527 in the same manner as in FIG. 19. Hose connector 516 is constructed and attached to member 517 in the same manner described with reference to FIG. 19. Front face 545 of member 517 is an ultra-flat lapped surface lying in a plane precisely at right angles to the axis of relative rotation established by bearings 526, 527.

Second swivel member 518 is generally like member 418, FIG. 23, but is entirely of stainless steel, so that rear face 552 is an ultra-flat lapped steel face lying in a plane precisely at right angles to the axis of relative rotation established by bearings 526, 527. Attachment of member 518 to the handpiece handle 515 is as described for the embodiment of FIG. 23.

Member 517 has a flow passage 530 for pressurized air, a central bore 532 for exhaust air, and two additional flow passages (not shown) for cooling water and cooling air. Rear face 552 of member 518 is provided with three circular grooves 555–557 concentric with the axis of relative rotation. A central bore 554 opens through rear face 552. A second bore 558, of a diameter larger than the radial width of groove 555, opens through the bottom wall of that groove. Two additional bores (not shown) open through the bottom walls of grooves 556 and 557, respectively. Bores 532 and 554 are coaxially aligned and in direct communication across the minute gap between spaces 545 and 552. As shown, the forward end of passage 530 opens directly into groove 555 so as to supply pressurized air into that groove and hence into bore 558. The other two flow passages (not shown) in member 517 are aligned respectively with grooves 556 and 557 in the same manner that passage 530 opens into groove 555, so that those passages deliver cooling water and cooling air respectively into grooves 556 and 557. Communication between the flow passages of swivel member 518 and the conventional ducting of the handpiece is established as described with reference to FIG. 23.

When member 517 has been installed, member 518 is installed in the same manner explained for FIG. 23, but with the axial location of member 518 precisely determined so that, when member 517 engages thrust bearing balls 526 and those balls engage flange 522, the desired minute space exists between faces 545 and 552. While the axial position of member 517 is not rigidly fixed, introduction of air and water under pressure from the hose bundle via connected 516 establishes a fluid pressure tending to separate the two swivel members, with the result that member 517 is urged against thrust bearing balls 526 and thus to a position precisely determined by flange 522. Casing 521 and members 517 and 518 can be machined with accuracy adequate to assure that the space between faces 545 and 552 during operation will be, for example, 10 millionths of an inch so that, while there is a gap between the two active faces, water cannot escape via that gap. While air can escape through some minute gaps which will not pass water, it is to be noted that escape of air in low volumes is not a significant disadvantage.

In all embodiments of the invention, it is advantageous to have bores such as bore 558, which open into a groove, be of a diameter which is larger than the radial width of the groove, since the larger diameter bore reduces total resistance to fluid flow. As shown in this embodiment, it is helpful to have grooves 555–557 of progressively smaller depths, i.e., the depth of groove 557 is smaller than that of groove 556, so that bores such as bore 458 can overlap the next adjacent groove without communicating therewith.

THE FIBER OPTIC EMBODIMENTS OF FIGS. 26–29

The invention has the advantage of being applicable to handpieces in which the tooth on which work is being done is illuminated via a fiber optic bundle. A particularly advantageous embodiment, in which light is conveyed through the swivel, is shown in FIGS. 26–28. Here, the device comprises casing 621, first swivel member 617, second swivel member 618, elastomeric gasket 619, and an adaptor 620 and nut 674 by which the device is secured to the end of handle 615 of the handpiece. Member 617 is mounted in casing 621 by bearings 676 and 677 in the same manner described with reference to FIG. 22, with bearing 676 securing the swivel member in a fixed axial position. Member 617 is of hardened stainless steel and has a ultra-flat lapped front face 645, a straight central through bore 610 and four flow passages 630, 632, 633 and 634. Swivel member 618 is a relatively thin circular disc of low friction polymeric material such as polytetrafluoroethylene having an ultra-flat lapped rear face 652 provided with four circular grooves 655a, 655, 656 and 657 concentric with the central axis of the disc. Member 618 also has a straight central through bore 611 of a diameter slightly smaller than that of bore 610 of member 617. The diameter of member 618 is, e.g., two or three thousandths of an inch smaller than the inner diameter of the surrounding portion of casing 621 so that bores 610 and 611 are at least nearly coaxial and all of the rear end of bore 610 is encompassed by the front end of bore 611. Grooves 655a–657 are of decreasing depths, from innermost groove 655a outwardly, as described with reference to FIG. 25, and member 618 has four bores each opening rearwardly through the bottom wall of each groove 655a–657 and each having a diameter greater than the radial width of the groove with which it communicates. Thus, bore 654 communicates with innermost groove 655a, bore 658 with groove 655, bore 659 with groove 656, and bore 660 with outer groove 661. Gasket 619 is engaged between the flat front face of member 618 and the rear face 676 of adaptor 620, the latter again being peripherally chamferred to provide an annular space into which elastomeric material of the gasket can flow as the gasket is compressed. Forwardly, adaptor 620 has male threads at 670 engaged with mating female threads on the casing so that, as the threads are made up with bearing 676 restraining member 617, faces 645 and 652 are urged into rubbing contact and gasket 619 is compressed between member 618 and adaptor 620. It will be understood that each of bores 654, 658, 659 and 661 communicates with a corresponding duct in the handpiece via conventional tubular shanks projecting rearwardly from handle 615 and received in forwardly opening recesses in the adaptor.

Input tubular shanks 637, 640, 642 and 643 are fixed directly to first swivel member 617 for attachment of the hose bundle and flow of air and water through the device occurs as described with reference to the embodiment of FIGS. 1-15 except that there is no fluid flow via through bores. Through bore 611 embraces a straight fiber optic rod or bundle 612 which passes forwardly through central through bores 611a and 611b in gasket 619 and adaptor 620, respectively. The rear end face of the fiber optic bundle is substantially coplanar with rear face 652 of member 618. Forwardly, bundle 612 leads into the handle of the handpiece and extends to a light emission point (not shown) adjacent the turbine in conventional fashion.

Disposed in bore 610 of the first swivel member 617 is a removable cartridge, indicated generally at 613 and comprising a sleeve 613a of insulating material, a cylindrical cartridge 613b carrying a lamp 613c, and the end of an insulated electrical conductor comprising insulating sheath 613d and two wires 613e connected to lamp 613c. Adjacent front face 645, the diameter of bore 610 is reduced, providing a small transverse annular shoulder 614 against which the front end of sleeve 613a is engaged so that cartridge 613 is so positioned that lamp 613c is spaced a small distance behind the end of fiber optic bundle 612, there thus being no rubbing contact between the envelope of the lamp and the end of the fiber optic bundle as members 617 and 618 turn relative to each other. Sleeve 613a closely embraces cartridge 613b and the end portion of insulating sheath 613d so that the sleeve, cartridge and conductor end constitute a unitary assembly which can be inserted in bore 610, during assembly of the device, and withdrawn from the bore, for repair or replacement. The insulated conductor is incorporated in the hose bundle. At its rear end, sleeve 613a is provided with an integral laterally projecting flat tab 613f, FIG. 27, detachably secured to the rear face of member 617, as by a screw as shown.

In the embodiment shown in FIG. 29, casing 721, first swivel member 717 and bearings 726 and 727 are the same as the corresponding parts in FIG. 21. Member 717 has a straight through bore 710. A hose connector 716 is rigidly secured to the rear end face of first swivel member 717, as by two screws as explained with reference to FIG. 23. Connector 716 is made in two halves 716a and 716b (the latter broken away for clarity of illustration in FIG. 26), each half presenting a flat face, as at 716c and the two halves being secured rigidly together, as by bonding the two flat faces together. Each flat face is provided with a groove 716d of semicircular transverse cross section so that, when the two halves of the connector are secured together, the two grooves combine to form a passage of circular transverse cross section having the same diameter as bore 710. Grooves 716d are of generally S-shaped plan form so that, in the completed connector, the passage includes a first straight portion at right angles to and opening through the rear face of the connector in a location spaced radially from the central axis of the connector and a second straight portion concentric with the central axis and opening forwardly through the front face of the connector so as to be coaxial with bore 710 in the assembled connector. A single fiber optic bundle 712 extends completely through the S-shaped passage defined by grooves 716d and forwardly through bore 710, the rear tip of bundle 712 projecting rearwardly from the rear face of connector 716, the front end face of bundle 712 being disposed at or a minute distance rearwardly from front face 745 of member 717.

Second swivel member 718, gasket 719, adaptor 720 and the frontal portion of casing 721 are identical to the same parts in the embodiment shown in FIG. 26. The central through bores of member 718, gasket 719 and adaptor 721 enclose a second fiber optic bundle 712a in the same manner described with reference to FIG. 26. The rear end face of bundle 712a is so located with respect to rear face 752 of member 718 that there is a minute space between the opposed ends of bundles 712 and 712a and no rubbing contact between the two fiber optic bundles occurs during relative rotation between the first and second swivel members. A light source is disposed at the rear end of bundle 712 in conventional fashion. Alternatively, though less advantageous, fiber optic bundle 712 can be extended to be part of the hose bundle. Fiber optic bundle 712a extends conventionally through the handpiece to the location at which light is to be emitted. Air and water flow passages are provided in the same manner described with reference to FIG. 26, save that adaptor 716 has passages as described with reference to FIGS. 2 and 19.

From a comparison of FIGS. 26 and 29, it will be apparent that the cartridge 613 of FIG. 26 can be made adequately flexible for installation in a curved passage, such as the passage formed by grooves 716d in the embodiment of FIG. 29.

What is claimed is:

1. For a dentist's installation of the type comprising a handpiece equipped with a turbine for driving a dental tool, a first flexible conduit for supplying pressure fluid to drive the turbine, a second flexible conduit for conducting exhaust fluid from the turbine, and at least a third flexible conduit for supplying cooling water to the tooth upon which work is being performed, the improvement comprising, in combination tubular casing means to be carried by the handpiece;
a first swivel member having
 a front face, and
 first, second and third flow passages opening through the front face;
bearing means operatively disposed between the casing means and the first swivel member and supporting the first swivel member for relative rotation between the casing means and the first swivel member about an axis at right angles to the front face of the swivel member, the bearing means comprising
 thrust means disposed to limit relative axial movement between the casing means and the first swivel member in a direction which would displace the front face of the swivel member rearwardly;
a second swivel member having
 a flat rear face, and
 first, second and third flow passages opening through the rear face,
 the second swivel member being disposed in the casing means with the rear face of the second swivel member facing the front face of the first swivel member;
means securing the second swivel member in the casing means in a position in which the front face of the first swivel member and the rear face of the second swivel member are separated by from zero to 0.0005 inch; and means secured against rotation relative to the casing means and second swivel member and providing separate passageways for communicating between the flow passages of the second swivel member and corresponding passageways of the handpiece;

at least one of said front face and said rear face being provided with a plurality of circular grooves concentric with said axis of relative rotation and opening toward the other of said front and rear faces, at least two of the flow passages of the first swivel member communicating with the corresponding passages of the second swivel member via respective ones of said grooves.

2. The combination defined in claim 1, wherein the second flow passage of the first swivel member and the second flow passage of the second swivel member are central bores which are coaxailly aligned and communicate directly with each other.

3. The combinatin defined in claim 1, wherein one of said front face and said rear face is of metal; and the other of said front face and said rear face is of low friction polymeric material.

4. The combination defined in claim 3, wherein said other face is a layer of polymeric material carried by and secured to the main body of the corresponding one of the swivel member,
said main body being of metal.

5. The combination defined in claim 4, wherein said main body, the other of the two swivel members, and the casing means are of metal having essentially the same thermal coefficient of linear expansion.

6. The combination defined in claim 3, wherein the second swivel member is an integral body of low friction polymeric material.

7. The combination defined in claim 1, wherein one of said first and second swivel members comprises a main body of metal and a face portion of low friction polymeric material secured thereto.

8. The combination defined in claim 1, wherein both of said front face and said rear face are of hardened stainless steel and both of said faces are lapped surfaces.

9. The combination according to claim 1, wherein the means securing the second swivel member in the casing means comprises an elastomeric gasket which is generally flat in its undistorted condition and has a rear face and a front face,
the elastomeric gasket being disposed within the casing means on the side of the second swivel member opposite the first swivel member,
the elastomeric gasket being embraced by the casing means and having a rear face engaging the second swivel member and a front face directed forwardly in the casing means; and a rigid member disposed within the casing means and secured to the casing means in a position such that the elastomeric gasket is compressed between the second swivel member and the rigid member, whereby the elastomeric gasket exerts a spring force urging the second swivel member rearwardly toward the first swivel member.

10. The combination defined in claim 9, wherein the rigid member comprises a rear outer portion which is threaded and engaged with internal threads on the casing means, and a front portion projecting forwardly from the casing means so as to be securable to the handpiece, the rigid member constituting the means providing separate passageways for communicating between the flow passages of the second swivel member and corresponding passageways of the handpiece.

11. The combination defined in claim 1, wherein the casing means includes an inner transverse annular forwardly facing race member;

the first swivel member comprises a larger diameter main body portion located forwardly of the race member of the casing means, a smaller diameter portion projecting rearwardly from the main body portion and through the opening defined by the race member of the casing means, and a transverse annular flange interconnecting the larger and smaller portions of the first swivel member, facing rearwardly toward the race member of the casing means, and defining a bearing race; and the thrust means of the bearing means comprises antifriction bearing elements operatively engaged between the race member of the casing means and the bearing race defined by the flange of the first swivel member.

12. The combination defined in claim 11, wherein the bearing means further comprises a plurality of radial antifriction bearing elements engaged directly between the main body portion of the first swivel member and the surrounding wall of the casing means.

13. The combination defined in claim 1, wherein
the first swivel member has a main body portion having a right cylindrical outer surface; and the bearing means comprises a plurality of needle bearing elements disposed for rolling contact with the cylindrical outer surface of the swivel member and the surrounding wall of the casing means.

14. The combination defined in claim 1, wherein
the first swivel member includes a right cylindrical outer surface portion formed with two axially spaced transverse annular outwardly opening bearing race grooves;

the casing means includes a right cylindrical inner surface portion surrounding the cylindrical outer surface portion of the first swivel member; and the bearing means comprises ball bearing elements disposed in said race grooves.

15. The combination defined in claim 14, wherein the thrust means of the bearing means is a thrust bearing provided in addition to the two bearings which comprise said ball bearing elements.

16. The combination defined in claim 15, wherein
the casing means presents a transverse annular inwardly extending shoulder portion adjacent the rearmost one of the two race grooves of the first swivel member; and the ball bearing elements disposed in the rearmost one of the race grooves coact with said shoulder portion in thrust bearing relation.

17. The combination defined in claim 16, wherein
the rearmost bearing race groove has a front wall, which faces generally rearwardly toward said shoulder portion of the casing means, and a rear wall;

the first swivel member includes a second right cylindrical outer surface portion commencing at and extending rearwardly from the rear wall of the rearmost bearing race groove and is of a diameter slightly smaller than the outer surface portion between the two bearing grooves; and the shoulder portion of the casing means has an inner diameter only slightly greater than that of said second outer surface portion of the swivel member.

18. The combination defined in claim 16, wherein the first swivel member projected rearwardly from the casing means, the combination further comprising a plurality of tubular hose connector shanks each carried by and projecting rearwardly from the first swivel member and each communicating with a different one of the flow passages of the swivel member.

19. The combination defined in claim 1, wherein the thrust means of the bearing means comprises a transverse annular inwardly extending shoulder portion carried by the casing means, and thrust bearing means operatively disposed between said shoulder portion and the first swivel member;

the first swivel member comprises a main body portion located forwardly of said shoulder portion, and a portion of smaller diameter than the main body portion, the portion of smaller diameter extending rearwardly through the annular shoulder portion of the casing means;

the combination further comprising a hose connector member located adjacent the annular shoulder portion of the casing means on the side of the shoulder portion opposite the thrust bearing means and rigidly secured to the smaller diameter portion of the first swivel member, strain applied in tension to the handpiece against the resistance of the flexible supply conduits being accepted by the thrust means.

20. The combination defined in claim 19, wherein the hose connectpr member has a frontal portion of larger diameter than the opening through the annular shoulder portion of the casing means, the combination further comprising second thrust bearing means operatively disposed between the hose connector member and the annular shoulder portion of the casing means.

21. The combination defined in claim 1, wherein the second swivel member is slidably embraced by the casing means;

the means securing the second swivel member in the casing means comprises means applying a rearwardly acting spring force to the second swivel member; and for each of the flow passages of the second swivel member which communicates with one of said circular groves, the transverse cross-sectional area of the flow passage is increased to expose to pressure of fluid flowing through the passage at least one surface portion of the second swivel member which faces forwardly and is approximately equal in area to the plan area of the one of said circular grooves with which the flow passage communicates, whereby the force occurring from pressure in the groove, which tends to separate the two swivel members, is counterbalanced by the force resulting from pressure of the fluid acting on said at least one surface portion.

22. The combination defined in claim 21, wherein each flow passage of the second swivel member which communicates with one of said circular grooves includes a forward portion of enlarged transverse cross section which opens through the front face of the second swivel member, the inner end of the forward portion being partially blind to provide said at least one surface portion.

23. The combination defined in claim 21, wherein the means applying a rearwardly acting spring force to the second swivel member is a substantially flat gasket having a rear face engaged with the front face of the second swivel member, there being a plurality of passages extending through the gasket and each communicating with a different flow passage of the second swivel member, each passage through the gasket having a larger transverse dimension than does the passage of the swivel member with which it communicates, whereby a portion of the front face of the second swivel member is exposed to the pressure within the passage of the gasket.

24. The combination defined in claim 21, wherein the means applying a rearwardly acting spring force to the second swivel member includes a force-applying member located forwardly of the second swivel member and having a rear face engaged with the front face of the second swivel member and a plurality of passages which open toward the front face of the second swivel member and each communicates with one of the flow passages of the second swivel member;

at least some of the flow passages of the second swivel member are of substantially constant diameter; and the corresponding passages of the force-applying member are of larger transverse dimension than said substantially constant diameter, whereby portions of the front face of the second swivel member are exposed to pressure in the passages of the force-applying member.

25. The combination defined in claim 24, wherein the force-applying member is an elastomeric gasket;

the means securing the second swivel member in the casing means further comprises means coacting with the second swivel member to maintain the elastomeric gasket under axial compression; and the transverse cross-sectional areas of the passages through the gasket are larger than the transverse cross-sectional area of the respective flow passages of the second swivel member when the gasket is so maintained under compression.

26. The combination defined in claim 1, wherein the second swivel member has a flat front face through which the flow passages of the second swivel member open forwardly;

the means securing the second swivel member in the casing means comprises a force-applying member located forwardly of the second swivel member and having a rear face engaging the front face of the second swivel member and passages opening through the rear face of the force-applying member to communicate with the respective flow passages of the second swivel member, and rigid means extending through an opening in the forceapplying member and within a forwardly opening blind bore in the second swivel member in a location displaced from said axis of relative rotation, the force-applying member and second swivel member being embraced by the casing means, said rigid means preventing relative rotation between the second swivel member and the force-applying member.

27. The combination defined in claim 26, wherein the force-applying member is an elastomeric gasket; the means securing the second swivel member further comprises a member embraced by the casing means forwardly of the gasket and engaged with the gasket to maintain the gasket under axial compression, said last-mentioned member having a rearwardly opening bore, said rigid means extending forwardly of the forceapplying member and within the rearwardly opening bore.

28. For a dental installation of the type comprising a handpiece equipped with a turbine for driving a dental tool, a first flexible conduit for supplying pressure fluid to drive the turbine, a second flexible conduit for conducting exhaust fluid from the turbine, at least a third flexible conduit for supplying a cooling fluid to the tooth upon which work is being performed, and fiber optic light means for illuminating the tooth, the improvement comprising, in combination tubular casing means to be carried by the handpiece and having a front portion directed generally toward the turbine and a rear portion directed away from the handpiece;

a first swivel member having
a front face,
first, second and third flow passages opening through the front face, and
an additional passage having a front end portion opening-through the front face in the center thereof;

a second swivel member having
a flat rear face,
first, second and third flow passages opening through the rear face, and
an additional passage having a rear end portion opening through the rear face in the center thereof,
the second swivel member being disposed within the front portion of the casing means and secured thereto against relative axial movement between the casing means and the second swivel member, the rear face being transverse to the casing means and directed rearwardly thereof;

means mounting the first swivel member in the casing means with the front face of the first swivel member opposed to and parallel with the rear face of the second swivel member and with the first swivel member and casing means being interrelated for relative rotation about an axis at right angles to the front and rear faces, the axis of relative rotation extending through the centers of the faces;

at least one of the front face of the first swivel member and the rear face of the second swivel member being provided with a plurality of circular grooves concentric with the axis of relative rotation and opening toward the other of said front and rear faces, the number of the circular grooves equalling the number of flow passages of the first swivel member, each of the flow pasages of the first swivel member communicating with the corresponding flow passage of the second swivel member via a different one of the circular grooves;

a fiber optic bundle disposed within the additional passage of the second swivel member,
one end of the fiber optic bundle being disposed at the rear face of the second swivel member and lying in a plane at right angles to the axis of relative rotation,
the fiber optic bundle extending forwardly to the handpiece; and means carried by the first swivel member and located in the additional passage of the first swivel member for supplying light forwardly to the fiber optic bundle disposed in the second swivel member.

29. The combination defined in claim 28, wherein the means carried by the first swivel member for supplying light is a lamp,
the combination further comprising
electrical conductor means extending into the additional passage of the first swivel member and electrically connected to the lamp.

30. The combination defined in claim 29, wherein the lamp forms part of a unitary replaceable assembly including
a sleeve having a front end portion in which the lamp is disposed and a rear portion embracing the electrical connector, the sleeve being embraced by the additional passage of the first swivel member.

31. The combination defined in claim 30, wherein the sleeve includes a laterally extending securing element detachably secured to the first swivel member.

32. The combinatin defined in claim 30, wherein the additional passage of the first swivel member is a straight bore.

33. The combination defined in claim 30, wherein the additional passage in the first swivel member includes a transverse shoulder adjacent the front face of the first swivel means; and
the sleeve is engaged with said shoulder to axially position the unitary replaceable assembly relative to the front face of the first swivel means so that the lamp is spaced slightly rearwardly of the front face.

34. The combination defined in claim 28, wherein the means carried by the first swivel member is a second fiber optic bundle.

35. The combination defined in claim 34 and further comprising
a hose connector secured to the first swivel member and having
a through passage opening forwardly at the center of the hose connector and rearwardly thereof in a location spaced radially from the center of the hose connector, the center of the hose connector being centered on the axis of relative rotation between the first swivel member and the casing means;

36. For a dental installation of the type comprising a handpiece equipped with a turbine for driving a dental tool, a first flexible conduit for supplying pressure fluid to drive the turbine, a second flexible conduit for conducting exhaust fluid from the turbine, and at least a third flexible conduit for supplying a cooling fluid to the handpiece for application to the tooth being treated, the improvement comprising, in combination
- a tubular casing to be carried by the handpiece and having a frontal portion and a rear portion,
  - the casing being of a material having a particular thermal coefficient of linear expansion;
- a first swivel member formed of a material having the same thermal coefficient of linear expansion as the material of the casing, the first swivel member having
  - a front face, and
  - first, second and third flow passages opening through the front face;
- a second swivel member formed of a material having the same thermal coefficient of linear expansion as the material of the casing, the second swivel member having
  - a rear face, and
  - first, second and third flow passages opening through the rear face,
  - the second swivel member being disposed in the casing with the rear face spaced forwardly from the rear portion of the casing and being secured against axial and rotational movement relative to the casing;
- means supporting the first swivel member in the casing for relative rotary movement between the first swivel member and the casing about an axis at right angles to said front and rear faces, said means including limit means opposing relative axial movement between the casing and the first swivel member,
  - the front face of the first swivel member and the rear face of the second swivel member being parallel, adjacent to each other, and opposed one to the other;
- at least one of said front face and said rear face being provided with a plurality of circular grooves concentric with said axis of relative rotation and opening toward the other of said front face and said rear face,
  - at least two of the flow passages of the first swivel member communicating each with the corresponding flow passage of the second swivel member via respective ones of the circular grooves;
- there being an axial gap between said front and rear faces which, during operation of the turbine of the handpiece, does not exceed 0.0005 inch.

37. The combination defined in claim 36, wherein said axial gap does not exceed 0.0005 inch.

38. The combinatin defined in claim 1, wherein the second swivel member includes a portion projecting forwardly from the casing means for attachment to the handle of the handpiece.

* * * * *